United States Patent [19]

Hänninen et al.

[11] Patent Number: 5,523,573
[45] Date of Patent: Jun. 4, 1996

[54] METHOD FOR THE EXCITATION OF DYES

[76] Inventors: Pekka Hänninen, Korkeavuorenkatu 2 B 25, FIN-20100 Turku; Erkki Soini, Krypingintie 20, FIN-21610 Kirjala, both of Finland

[21] Appl. No.: 365,412

[22] Filed: Dec. 28, 1994

[30] Foreign Application Priority Data

Jan. 26, 1994 [FI] Finland ............................ 940374

[51] Int. Cl.$^6$ ................................................ G01N 21/64
[52] U.S. Cl. ............................................ 250/459.1
[58] Field of Search ......................... 250/458.1, 459.1, 250/461.2

[56] References Cited

U.S. PATENT DOCUMENTS

| | | | |
|---|---|---|---|
| 4,791,310 | 12/1988 | Honig et al. | 250/461.2 X |
| 4,877,965 | 10/1989 | Dandliker et al. | 250/461.2 X |
| 5,034,613 | 7/1991 | Denk et al. | 250/458.1 |

OTHER PUBLICATIONS

Warner L. Peticolas, et al., *Physical Review Letters*, 15 Jan. 1963, vol. 10, No. 2, pp. 43–45.
M. J. Wirth et al., *Anal. Chem*, 1990, vol. 62, No. 9, May 1, 1990, pp. 973–976.
Winfried Denk, et al., *Science*, vol. 248, 6 Apr. 1990, pp. 73–76.

Primary Examiner—Carolyn E. Fields
Assistant Examiner—Edward J. Glick
Attorney, Agent, or Firm—Ronald J. Kubovcik

[57] ABSTRACT

A method for the two-photon excitation of long-lived fluorescent or phosphorescent dyes with long low-power pulses. In the method time-resolved detection is used to detect long-lived dyes. In the method long-lived dyes are excited to the excited state with light pulses of long duration via double-photon absorption. In the two-photon absorption process the chromophor of the dye molecule is excited through the summation of the energies of two or more photons when they are simultaneously absorbed. As the method is based on the use of pulses of long duration and on time-resolved detection the peak power of the pulses may be kept low. Long pulses of low power can be produced with a great variety of low-power light sources. The light source may in this case be e.g. a semiconductor laser. The excitation technique according to the invention may exploit the doubling or multiplication of the excitation wavelength or the nonlinearity of the two-photon absorption process. The method may be used for the detection of the fluorescence or phosphorescence from long-lived dyes for the determination of biospecific binding in applications of analytical or microscopic methods.

12 Claims, 6 Drawing Sheets

METHOD FOR THE EXCITATION OF DYES

BACKGROUND OF THE INVENTION

This invention relates to a method for the excitation of long-lived fluorescent and phosphorescent dyes.

The publications and other materials used herein to illuminate the background of the invention, and in particular, cases to provide additional details respecting the practice, are incorporated by reference.

The method according to this invention allows the excitation of dyes emitting long-lived fluorescence and phosphorescence, with light of a wavelength considerably longer than their normal excitation wavelength. In the method according to the invention the dyes are excited by so-called two-photon excitation, the excitation resulting from the summation of the energies of two photons. The method according to this invention is applicable to fluorescent or phosphorescent dyes with an emission half-time longer than 100 ns due to an intermediary energetic triplet state. These dyes consequently have considerably longer half-times of excitation states than the emission half-times of ordinary organic dyes. The emission half-time of organic dyes is usually 1–10 ns, maximally 100 ns because emission usually does not occur via an intermediary triplet state.

These fluorescent and phosphorescent dyes are used in biospecific assays as molecular labels. Examples of the most widely used biospecific assay techniques are the immunoassay and the DNA hybridization assay. Binding of antibody is assayed by measuring the emitted light. Biospecific assays are used in in vitro diagnostics as well as in microscopy. In microscopy antibodies allow the detection and localization of e.g. the structural elements of micro-organisms.

Two-photon excitation of short-lived fluorescent molecules is a well-known technique e.g. in the fields of spectroscopy and microscopy. The said method requires, with current technology, high-energy laser instruments producing ultra-short pulses. Two-photon excitation is possible with a high momentary photon density. Simultaneous absorption of two photons is then probable. A high photon density is achieved by high luminous energy and by optical focusing of the light. Two-photon excitation has been described theoretically as early as 1931 (Göppert-Mayer, M. Ann. Phys. 1931, 9:273). The first prooves of the functionality of the method were obtained in the 1960's when laser instruments became available. In 1963 the first two-photon excitation in organic crystals was reported (Peticolas W. L., Goldsborough J. P., Reickhoff K. E. Phys. Rev. Let. 1963, Vol. 10/2). Two-photon excitations may also be observed with continuous high-energy laser radiation (Sepaniak M. J., Yeung ES. Anal. Chem. 1977, 49:1554–1556), but in this case the scattering of excitation light and heating of the sample interfere severely with measurement.

The advantage of two-photon excitation lies in the fact that visible light can be used for excitation instead of UV excitation. When visible light is used in order to elicit emission by exciting the dye by two simultaneous photon pulses, the scattering of light is reduced considerably as compared to excitation by UV radiation. In addition, two-photon excitation reduces damage caused by light to the sample below and above the object under examination. Two-photon excitation is best suited for the examination of small sample volumes or structures.

When applied to scanning microscopy, two-photon excitation allows a three-dimensional resolution comparable to the confocal microscope, without the second pinhole required in the confocal microscope. The method has been described in U.S. Pat. No. 5,034,613; 1991. The delimitation of the excitation in the three-dimensional space has been described in the literature (Anal. Chem. 1990, 62:973-976; Science, 1990, Vol. 248:73-76).

It is well known that the absorption of a single photon in a dye is, according to the concepts of probability, an independent event. The absorption of photons is a series of single, independent events. The probability of the absorption of a photon may be represented by a linear function. Absorption is linear as long as the energy states to be excited are not filled. It is known that the absorption of two or more photons is a nonlinear process (U.S. Pat. No. 5,034,613). When two or more photons are absorbed the absorption of single photons is no longer independent. A dye is excited only upon simultaneous absorption of all photons. The probability of the absorption of several photons is equal to the product of the probabilities of absorption of single photons. The emission caused by two photons is thus an exponential function to the power of two, the emission caused by three photons an exponential function to the power of three, etc.

The properties of an optical system for microimaging may be described by considering the response of the system to a point-like light source. A point-like light source forms, due to diffraction, an intensity distribution, characteristic of an optical system, in the focusing point (point response). This intensity distribution further reflects the resolution of the system. When normalized, this intensity distribution constitutes a probability distribution of the photons emitted from the point-like light source and hitting the focusing area. The nonlinear nature of two-photon absorption can be exploited to improve resolution. The probability distribution of two-photon excitation is then the normalized product of the intensity distributions of the first and the second photon. A probability distribution obtained in this way is clearly more delimited in the 3-dimensional space, especially in depth, than the probability ditribution of a single photon. Consequently, with two-photon excitation only the fluorescence generated in the clearly delimited, three-dimensional immediate vicinity of the focal point is detected (U.S. Pat. No. 5,034,613). The system is thus in its principle similar to the more traditional 3-dimensional optical microscope, or confocal microscope. In the confocal microscope the point response of the system is the normalized product of the probability distributions of point-like excitation and point-like detection (Confocal Microscopy, T. Wilson (ed), Academic Press, London, 1990, 1–64).

Figure 1A:
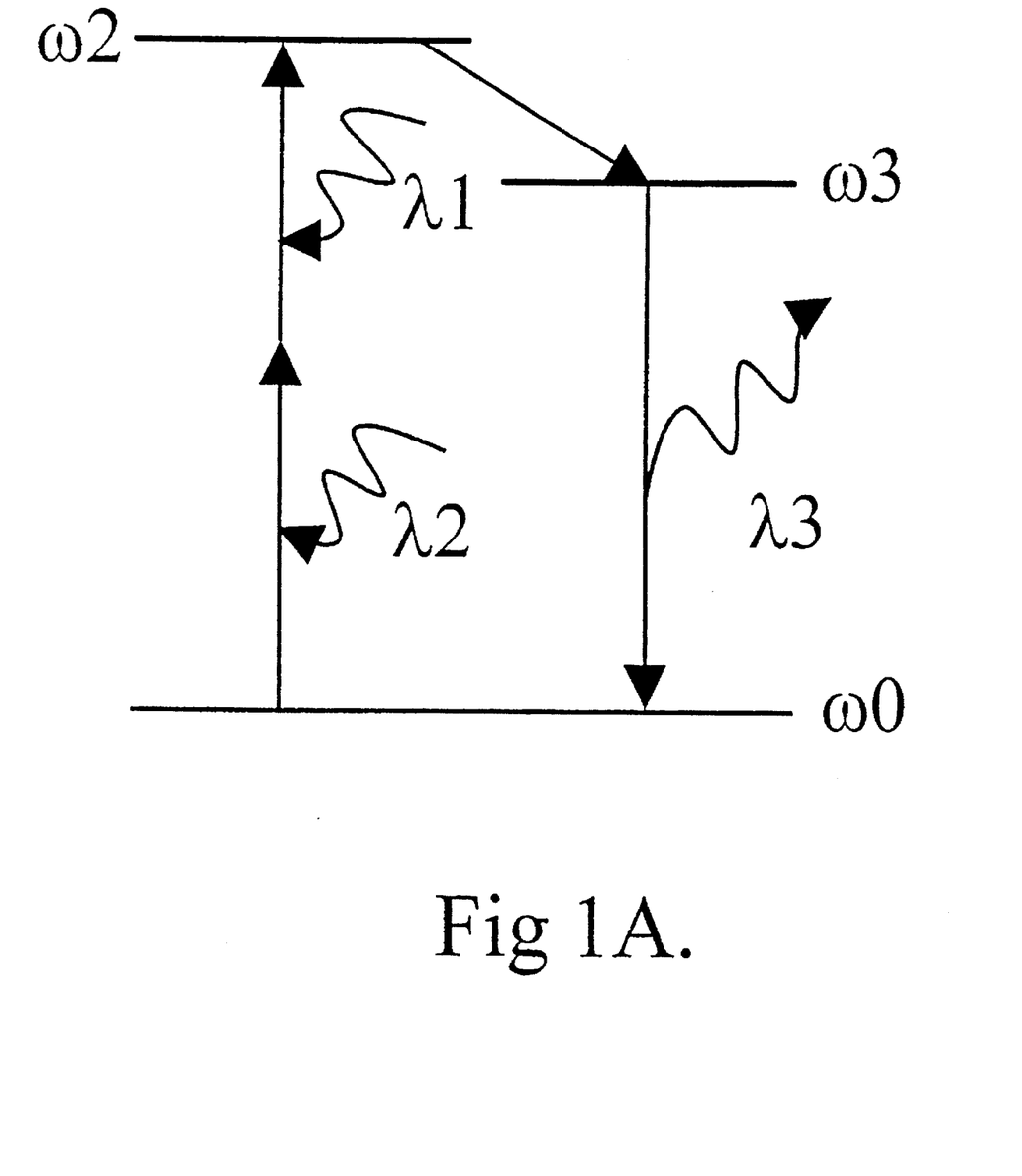
FIGS. 1A and 1B illustrate schematically the principles of two-photon excitation
Figure 1B:
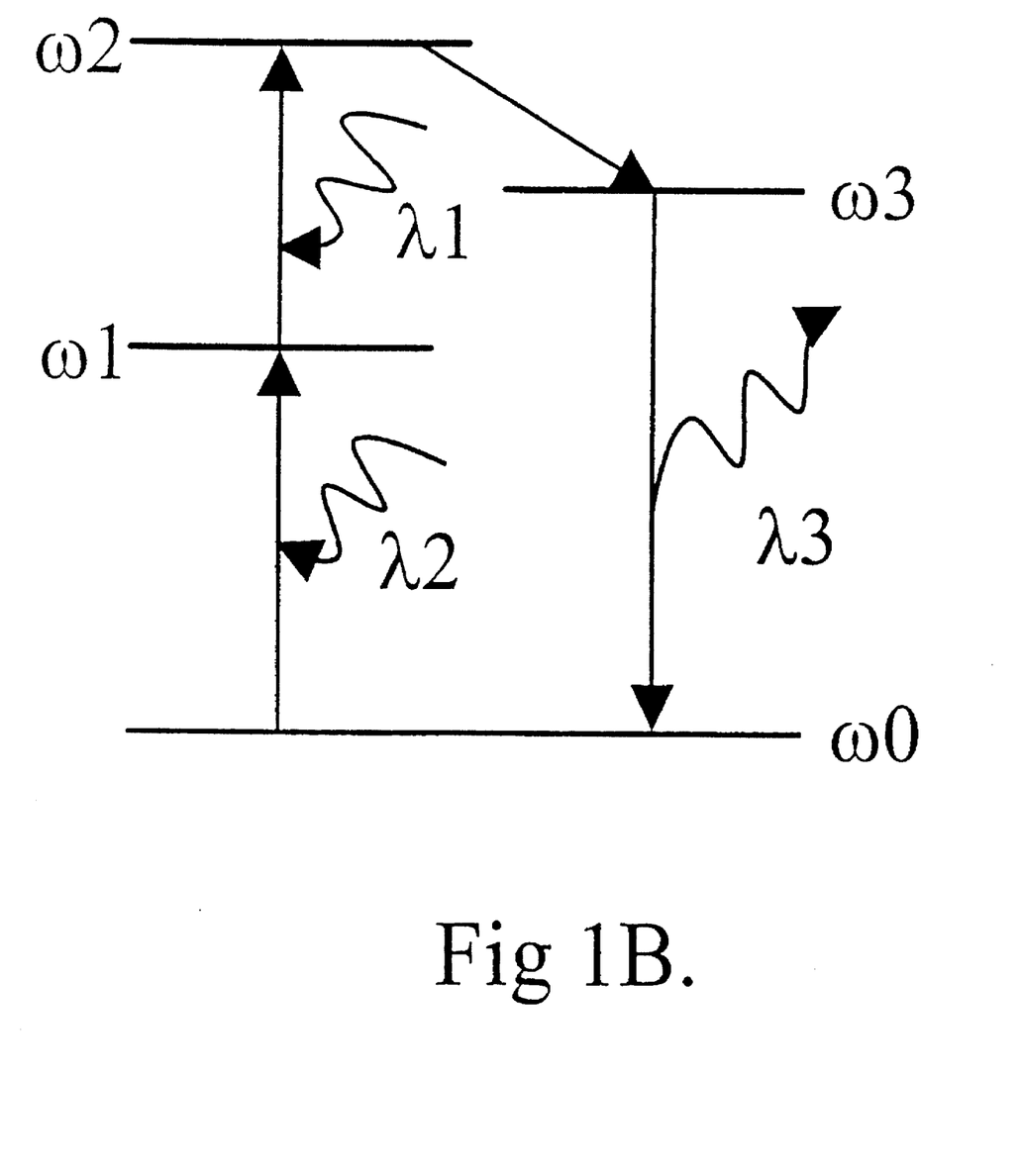

In order for the two photons to absorb, the dye must absorb the photons in such a way that the total sum of the energies of the photons equals the energy required for excitation (FIG. 1). The excitation then proceeds either via the intermediary energy state (omega 1) of the electrons of the molecule or directly to the excitation state (omega 2). The different possibilities of double-photon excitation are displayed in FIGS. 1A and 1B: in Figure A, directly as the combined result of two photons (lambda 1 and lambda 2); in Figure B, via the intermediary energy state (omega 1). Excitation via an intermediary state (FIG. 1B) requires a dye having such an intermediary energy state. Direct excitation of two photons according to FIG. 1A requires no intermediary state, instead the photons must absorb simultaneously, within approximately $10^{-15}$ seconds, in the same chromophor of the dye.

A disadvantage of current systems based on two-photon excitation is the cost of the extremely high-power pulsed laser and the large size and complexity of the equipment. A continuous laser requires continuous power of several watts. This destroys nearly all known organic samples. A further disadvantage is the scant amount of emitted light compared to excitation light, and scattering of excitation light in addition interferes with the detection of the emission from ordinary short-lived dyes.

The excitation states of excited dyes discharge their energy in an exponential relation according to equation [1]:

$$N=N_0 exp(-t/tau) \qquad [1]$$

N is the number of discharging molecules at a given time point, $N_0$ is the number of molecules discharging at time point=0, and tau is the average life-time of the excitation states ("decay parameter"). In the following discussion the terms long-lived and short-lived dyes are used to designate dyes with a long (100 ns–10 ms) or a short (1 ns–100 ns) average life-time tau.

Time-resolved detection of long-lived dyes involves the use of pulsed light for the excitation of the dye, and detection is started after a delay with respect to the excitation pulse. Detection is typically by photon counting, the counting being done within a specified time window. When detecting lanthanide chelates the photons are counted within e.g. 0.1–1 ms after the termination of the excitation pulse.

It is well known that time-resolved fluorescence detection of long-lived fluorescent dyes allows a sensitivity greater by several orders of magnitude than is possible in the detection of short-lived fluorescent molecules. The said molecules have allowed e.g. partial replacement of radioisotopes in immunodiagnostics and improvement of the sensitivity of detection (Soini, Lövgren. CRC Crit. Rev. Anal. Chem. 1987, 18:105–154).

Also in microscopy time-resolved detection of long-lived fluorescence allows reduction of background and thus greater sensitivity (Seveus et al. Cytometry, 1990, 13:329–338).

Long-lived fluorescence required in time-resolved detection is a property of e.g. the ions $Eu^{3+}$, $Sm^{3+}$, and $Tb^{3+}$ of the lanthanide group. In inorganic compounds, the absorption properties of these metals are quite inferior, but when an organic ligand is linked to the metal, absorption can be improved considerably. In these so-called lanthanide chelates the photon to be excited is absorbed in the organic ligand, from which the excitation energy is transferred to the lanthanide ion. The excitation of all known lanthanides occurs in UV area 250 nm–370 nm. The structure and use of lanthanide chelates has been described by e.g. Ilkka Hemmilä in his book: Applications of Fluorescence in Immunoassays: 7.4.1 (140–145), John Wiley & Sons, N.Y., 1991.

A known disadvantage of UV-excited long-lived dyes like the lanthanide chelates is the scattering of light in the UV area, which interferes with the detection of emission. Also the manufacturing of UV-transparent components functioning correctly with UV light is difficult. Neither is the functioning and stability of the flashlamps currently used in immunoassays satisfactory in all respects. Consequently, it will be advantageous to design a system capable of employing excitation light of longer wavelength.

When ultrashort pulses (<1 ps) described in U.S. Pat. No. 5,034,613 are used for two-photon excitation, the life-time of the dye is without significance because the life-time of the short-lived or long-lived light-emitting dyes is in any case longer by orders of magnitude than the life-time of the exciting pulse. During the ultrashort pulse the energy states will be excited independently of the life-time of the emission of the dye. Ultrashort pulses are advantageous when using short-lived fluorescent molecules, as they allow control of average energy and damage to the sample. The scattering of light detected by the measuring instruments is also the least with ultrashort pulses. The dependence of the fluorescence intensity (I) obtained with two-photon excitation, on the excitation mechanism may be modelled by the equation:

$$I=Constant*P^2 t \qquad [2]$$

P is the maximum power of the pulsed excitation light, and t is the duration of the pulse. The constant is dependent on the optical system and the dye used. This principle has been described in the literature (Wirth, Fatumbi. Anal. Chem. 1990, 62:973–976). This principle can also be deduced by the methods of probability calculation.

In two-photon excitation of short-lived molecules the objective is to achieve as short pulses as possible, of maximal power, to keep the energy of the pulses according to equation [2] as low as possible.

BRIEF SUMMARY OF THE INVENTION

The characteristics of the invention are shown in claim 1.

In the method according to this invention the objective is to realize two-photon excitation without course to the use of ultrashort laser pulses. The essence of this invention lies in the observation that the emission generated from two-photon excitation of long-lived fluorescent and phosphorescent dyes can be detected by time-resolved methodology without interference from the scattering of the excitation light. The long life-time of the fluorescence or phosphorescence also allows the use of longer excitation pulses and correspondingly lower excitation power. In the linear single-photon excitation the use of pulsed light allows straight-forward reduction of the peak power of the pulse, the peak power of the pulse being inversely related to the duration of the pulse. In two-photon excitation the peak power of the pulse can be reduced so that the peak power of the pulse according to equation [2] in this case is inversely related to the square root of the duration of the pulse.

In two-photon excitation time-resolved detection is performed in the same way as in normal time-resolved detection. A long-lived dye is excited via double-photon absorption with a pulse shorter or at the most as long as the life-time of the dye in question, in the case of lanthanide chelates (tau=1 ms) e.g. 0.1–1 ms). The start of detection is delayed as in normal time-resolved detection, and the measurement is performed in a time-window appropriate to the dye used.

BRIEF DESCRIPTION OF THE DRAWINGS

The invention is described in the following section by reference to the adjoining illustrations in which.

DETAILED DESCRIPTION OF THE PREFERRED EMBODIMENTS

The mathematical modelling of the principle of this invention is best performed by applying equation [2] in another form:

$$P_1^2 t_1 = P_2^2 t_2 \qquad [3]$$

The two sides of the equation [3] describe the relation of the peak powers of the two pulses (pulse 1 and pulse 2) to the duration of the pulses, under the assumption of unaltered number of two-photon excitation events. An example in U.S. Pat. No. 5,034,613 describes the two-photon excitation of a short-lived dye (life-time<10 ns). In the example an average power of 50 mW, pulse duration of 100 fs and repetition frequency of 80 MHz were calculated. The peak power then is 6.2 kW. The theoretical calculation has been verified by actual measurement to be of the correct order of magnitude. In the method according to this invention the assumption may be made that the absorption parameters of a long-lived dye are the same as in the example of the U.S. Pat. No. 5,034,613, and according to equation [3] a pulse with a power of 200 mW and a duration of 0.1 ms allows the attainment of the same intensity of two-photon fluorescence than a pulse with a power of 6.2 kW and a duration of 100 fs. In the fluorescence detection of short-lived dyes this kind of consideration is merely theoretical, because with dye life-times of the order of a few nanoseconds the duration of the excitation pulses could be at the most of the same order to allow identification of the photons generated in fluorescence, as distinct from the excitation pulse. Time-resolved detection of a dye with a half-life of 1 ms allows an excitation pulse of 0.1 ms in order to avoid any significant interference by the duration of the pulse with the time-resolved detection of two-photon fluorescence. The said methodology thus allows two-photon excitation of long-lived dyes with low pulse peak power. The sensitivity, higher by several orders of magnitude, attainable with time-resolved detection allows the reduction of the peak power of the excitation pulse. The method according to this invention consequently allows the detection of two-photon-excited long-lived fluorescence or phosphorescence with a power of the excitation pulse of a few milliwatts. In practice the duration of the pulse to be used can be optimized according to a specified peak power. When the duration of the pulse approaches the half-time of the emission from the dye used equation [2] is no longer valid because during excitation a proportion of the excitation states discharge according to equation [1]. When the energy states of the dye are not filled the optimal duration of the pulse is usually of the same order than the half-time of the emission from the dye. With longer duration of the pulse the energy transferred to the sample also increases, in which case care must be taken not to damage the sample. If needed, shorter duration of pulse or lower repetition frequency of excitation pulses is selected.

Figure 2:
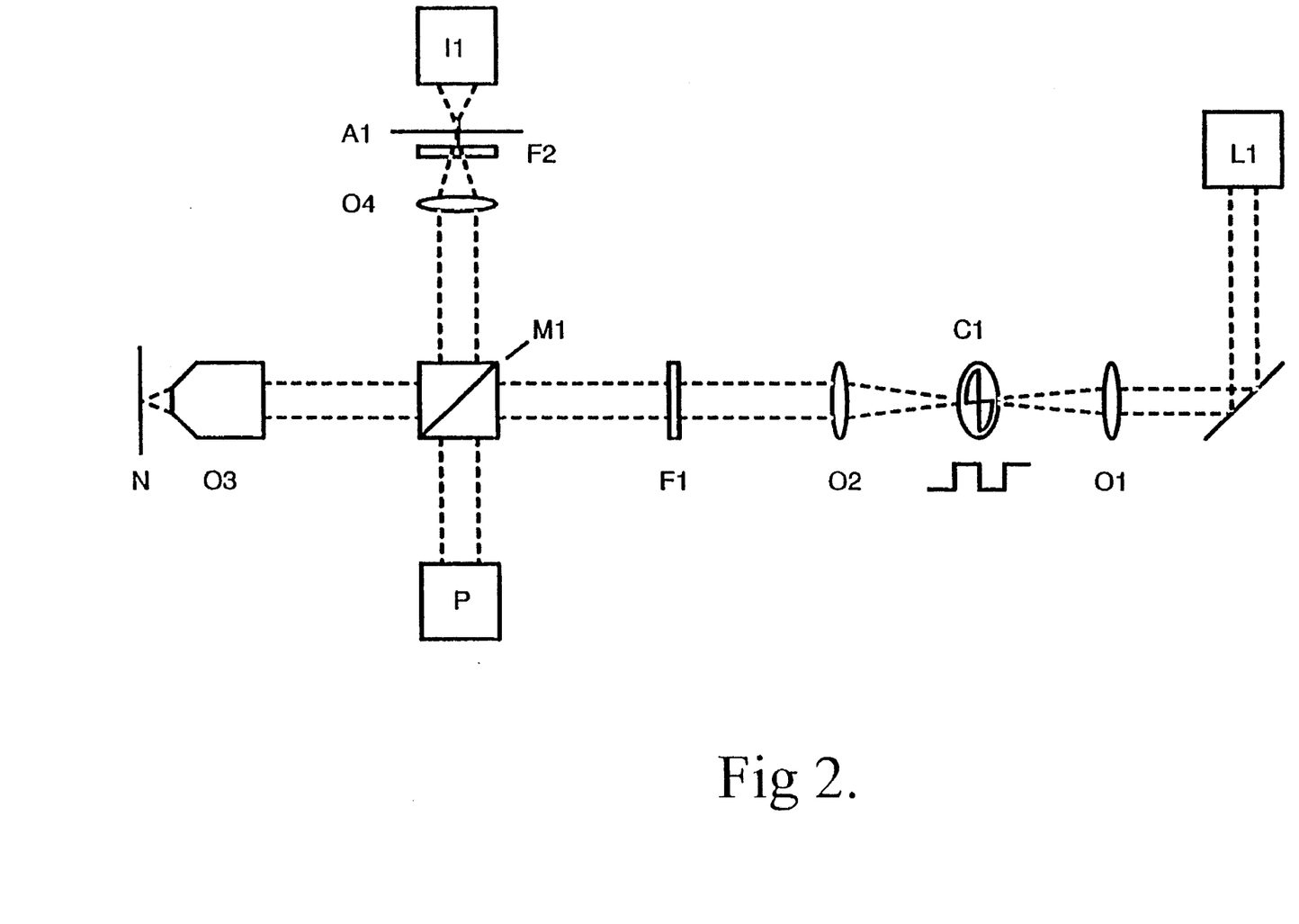
FIG. 2 represents the instrument constructed according to the invention for the testing of the method FIG. 3 displays the measurement function obtained with the method according to the invention, which function allows the demonstration of the applicability of the invention FIG. 4 gives an example of the application to immunoassay of the method according to the invention FIG. 5 gives an example of the application to microscopy of the method according to the invention
Figure 3:
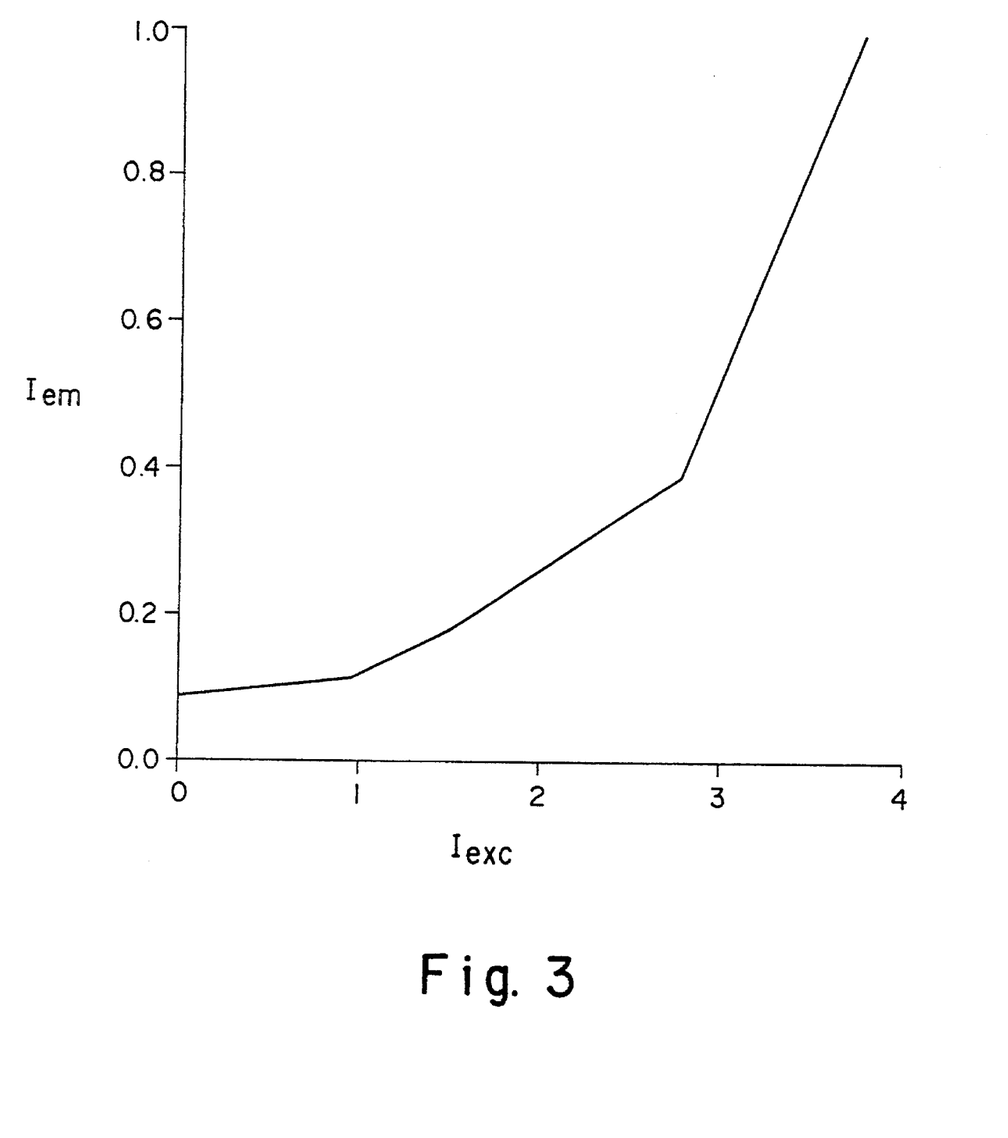

For the testing of the operation of the method according to this invention measuring instrumentation was constructed as illustrated in FIG. 2. The sample used was a crystal of yttrium oxysulphide activated with europium ($Y_2O_2S_2$:$Eu^{3+}$), whose emission half-time is approximately 0.7 ms and the wavelength of maximum absorption approximately 300 nm. The light source L1 was an argon-krypton mixed gas laser used at the wavelength of 647 nm. The excitation light was converged with lens O1 onto revolving shutter C1 and further diverged to make it parallel, with lens O2. The monochromatic quality of the excitation light was assured with excitation filter F1. Beam divider M1 divided the light of the excitation pulse between power monitor P and the object to be excited N. The division ratio at the wavelength used was about 15% to the power monitor and about 85% to the object to be excited. Beam divider M1 is made of quartz and thus emits no interfering long-lived fluorescence of its own. Microscope objective O3 was used to focus the beam of light onto sample crystal N. The emission from the sample was returned via objective O3 to beam divider M1. M1 deflected 15% of the emitted light to the direction of detector I1. To reduce diffused light the emitted light was focused onto aperture A1 with lens O4. Emission filter F2 was placed in front of the aperture. The bandpass of the emission filter is 616 nm±8 nm. Photon counting with photomultiplier I1 was used for detection, and counting was restricted to a time window of 200 µs–1 ms after the termination of the excitation pulse. A constant number of pulses and counts were repeated until the signal could be distinguished from background with sufficient efficacy. Excitation intensity was modified for the testing of the two-photon excitation. FIG. 3 illustrates the detection of the emission from a crystal of $Y_2O_2S_2$:$Eu^{3+}$. The x-axis represents excitation intensity ($I_{exc}$) and the y-axis the fluorescence signal emitted ($I_{em}$), respectively. The maximum peak power of excitation in the sample was in this case lower than 5 mW. The detection was repeated with several crystals. The repeated detection results were similar within the margin of error. The result displayed in FIG. 3 shows the nonlinear relation of the emission to excitation intensity. FIG. 3 allows description by equation [2] within the limits of the margin of error and the background in the detection.

To summarize, it may be stated that the method according to this invention allows e.g. the two-photon excitation of lanthanide chelates with a low-power light source, when fluorescence is detected with time-resolved methodology. As excitation is performed with visible light and a pulse with low peak power the instrument is economic and easy to use. The said invention further allows the use of lanthanide chelates having an excitation maximum in the region of 270 nm–330 nm. This short-wavelength UV region presented formerly little possibility for exploitation because conventional optic materials and components do not function in this wavelength region.

The method according to the invention can be used in biospecific assays by replacing UV excitation formerly required by fluorescent or phosphorescent dyes by excitation with visible light, the excitation in this case being based on two-photon excitation. The pulse power required being low, in practice, the cost of the instrumentation can be contained.

In biospecific assays the method according to the invention further allows the delimitation of the size of the area to be excited and consequently the reduction of background fluorescence which interferes with detection. The accuracy and sensitivity of the detection can thus be improved.

In microscopy, the method according to the invention further extends the applicability of long-lived fluorescent and phosphorescent dyes. With a scanning microscope 3-dimensional resolution can be attained without resorting to a complex instrumentation, and the imaging properties of the microscope can be improved by performing the imaging process in the best spectral area of current microscope optics. In addition, damage caused to the sample by light is reduced, as use of UV light can be avoided.

The method according to the invention can also be used in other types of time-resolved detection systems where the nonlinear two-photon procedure may present advantages.

The method according to the invention can be extended to include excitation by three or several photons. The required peak power will then be higher but the sensitivity of time-resolved detection still allows use of modest intensities. It should be noted that the term "two-photon excitation" employed in this patent application shall be understood to designate multi-photon excitation in general, two-photon excitation being the most widely used method and the easiest to realize.

The method according to the invention can also be used with long-lived dyes other than lanthanide chelates. Examples of such dyes are phosphorescent metalloporphyrins or fluorescent cryptates.

As the powers required in the method according to the invention are low with long pulse duration, other light sources are possible in addition to lasers. Other light sources could be e.g. high-power xenon discharge lamps. When using a xenon discharge lamp, a specified spectral band, instead of one wavelength, can be employed for excitation, corresponding to the absorption band of the two-photon excitation of the dye.

In the method according to the invention the laser instrument may be e.g. an air-cooled continuous krypton ion laser whose krypton band of 647 nm can be used to excite a 323.5 nm state by two-photon excitation. Semiconductor lasers for the region 600 nm–1300 nm are also currently available, whose energy is sufficient for two-photon excitation of long-lived dyes.

Figure 4:
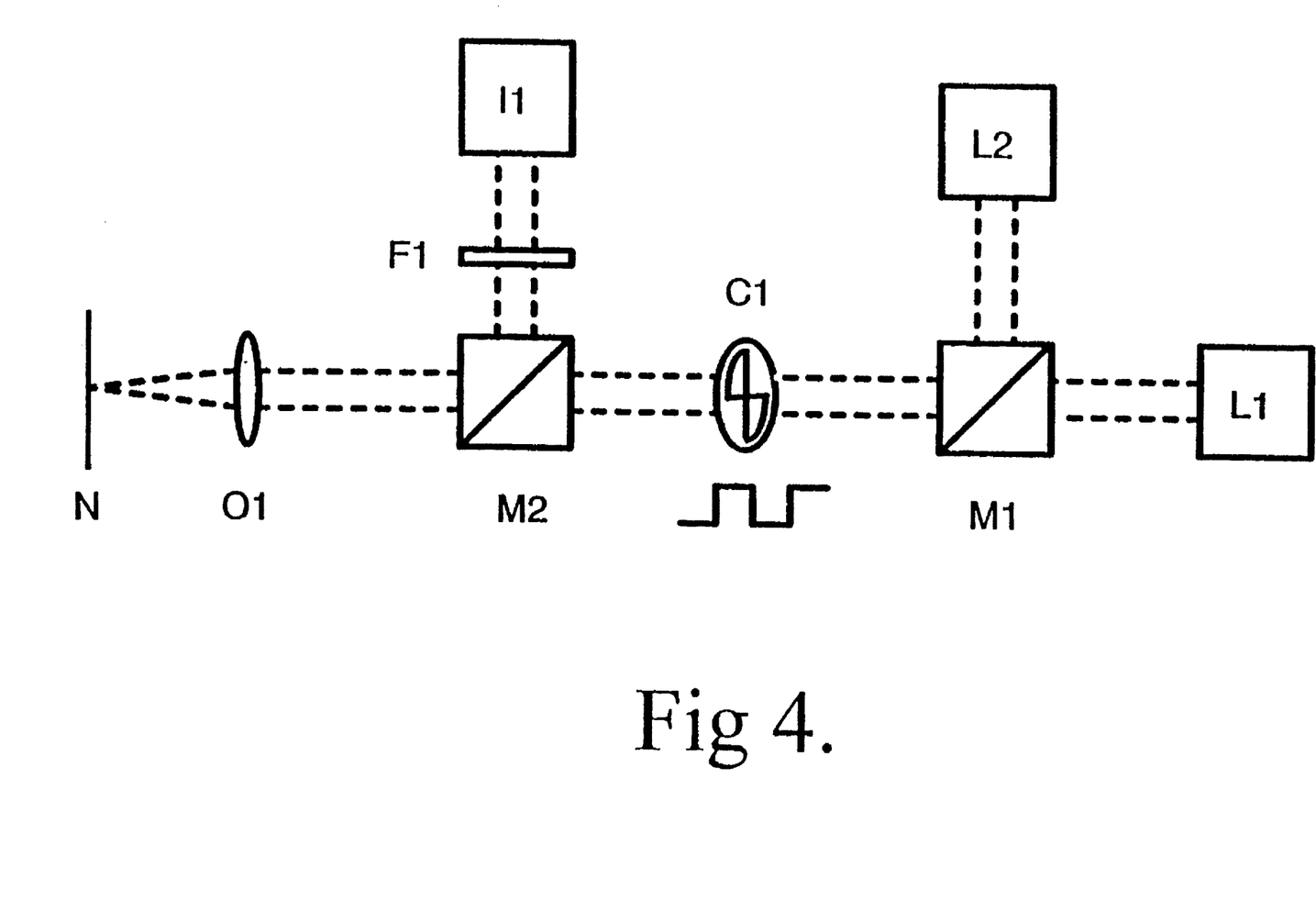

In biospecific assays the method according to the invention can be exploited e.g. in an instrument like the fluorometer illustrated in FIG. 4. Light source L1 and light source L2 are converged with dichroic mirror (beam divider) M1 to form a light pencil. The light sources L1 and L2 should preferably be point-like, which allows the maintenance of their peak power at a low level. L2 and M1 may be omitted if desired, as two-photon excitation can be performed with just one light source. The light pencil is chopped with optic chopper C1 to generate the pulse required for time-resolved detection. When a pulsed light source is used C1 may be omitted. The pulse-shaped light pencil is focused with lens O1 onto sample N. The long-lived emission light is returned via lens O1 and resolved with dichroic mirror M2 and emission filter F1 from the wavelength of the excitation light. The time-resolved detection is performed with detector I1, delaying detection until the background signal is sufficiently low. Detector I1 may be e.g. a photomultiplier tube or any other photodetector. This description of the instrument shall be understood to be given as an example only.

In microscopy, the method according to the invention may be exploited by an instrument according to FIG. 4 in its principle, in which instrument lens O1 is replaced by an objective suitable for microscopy, and sample N is replaced by a microscopic sample, respectively. Light sources L1 and L2 must be point-like also in this case. In order to form an image, either the sample A1 must be moved after detection of each point or the beam must be deflected. The structure of a scanning microscope has been described e.g. in Confocal Microscopy, T. Wilson (ed.), Academic Press, London, 1990 (1–64). The image is formed with an instrument, e.g. a computer registering detected signals.

Figure 5:
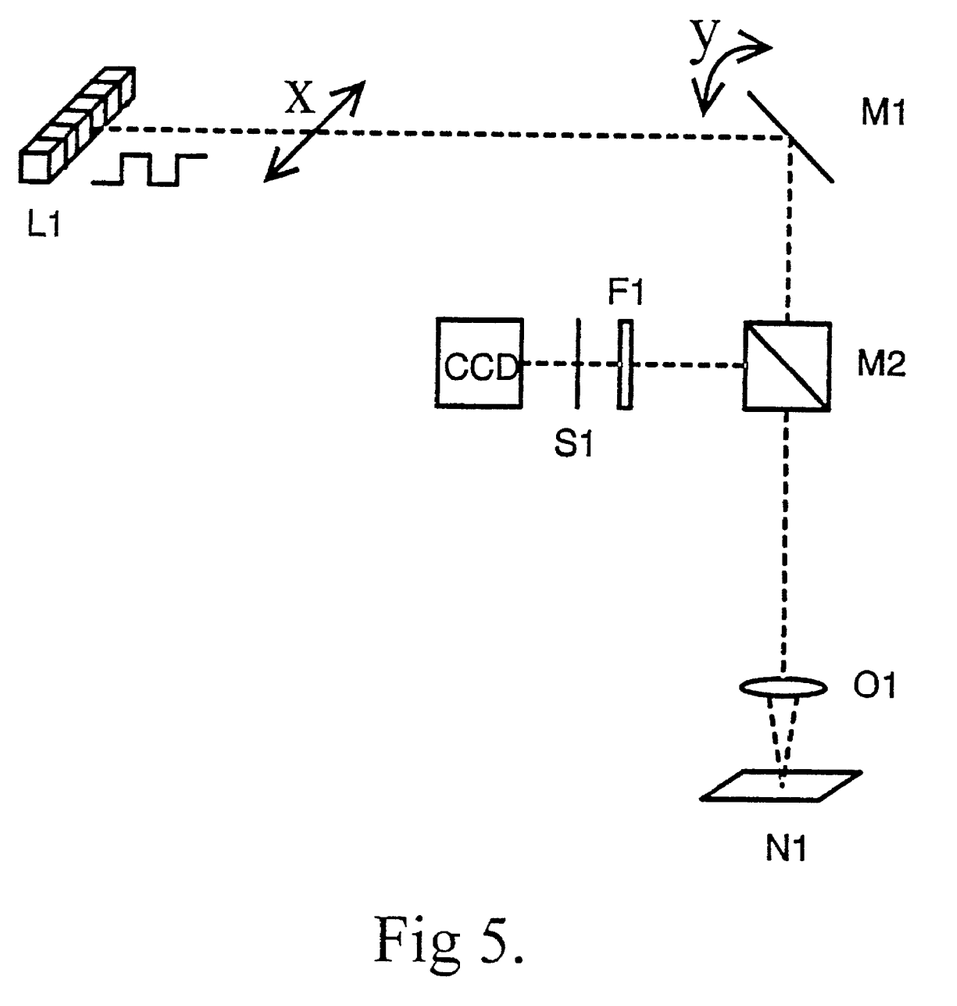

An excellent way of exploiting semiconductor technology and the method according to this invention has been described in FIG. 5. The point-like light source has been replaced with a beam-like light source. This light source may be e.g. a semiconductor laser array or matrix. Other light sources, which are focused onto a narrow slit with e.g. a cylindrical lens, may also be used. The semiconductor laser is, however, the most economical to use, because the power required may be increased simply by increasing the number of the light-producing elements. In the system according to FIG. 5 the pulsed beam-like light source L1 is deflected with mirror M1 and focused with objective O1 to generate a beam-like excitation band in sample N1. If a matrical light source is used, deflection is unnecessary. The emission light is resolved from the excitation light with dichroic mirror M2 and focused onto the surface of a CCD element via emission filter F1 and shutter S1. Deflection of the excitation band results in a different storage site of the emission on the surface of the CCD element. The entire image area generated when the excitation band is deflected across the image area is integrated in the CCD element. In the time-resolved methodology the light hitting the CCD element is chopped with shutter S1. S1 may be operated mechanically or electrically. The said instrument corresponds in some of its constituents to the bilateral confocal microscope described in literature (Brakenhoff, Visscher. J. Microsc. 1992, 165:139–146). In the bilateral confocal microscope pinholes are replaced with a narrow slit, and scanning is performed in a bilateral manner with one mirror, the front side of the mirror deflecting the exciting narrow slit in the sample and the back side of the mirror deflecting the detection slit on the CCD element. In the system described in FIG. 5 the bilateral scanning using the two sides of the same mirror is unnecessary, due to the nonlinear excitation process, which makes the instrument simpler, allowing a greater amount of emission light to be detected.

The examples for microscopy shall be understood to represent examples only. The method according to the invention may be exploited also in other systems applicable to microscopy.

It will be appreciated that the methods of the present invention can be incorporated in the form of a variety of embodiments, only a few of which are disclosed herein. It will be apparent for the artisan that other embodiments exist and do not depart from the spirit of the invention. Thus, the described embodiments are illustrative and should not be construed as restrictive.

We claim:

1. A method for multi-photon excitation of a dye, comprising
   (i) irradiating a dye with a long duration light pulse from a low power light source, thereby exciting said dye via multi-photon absorption,
   (ii) detecting fluorescence or phosphorescence emission from said dye via a time-resolved technique.

2. The method according to claim 1, wherein said emission has an average life-time of at least 0.1 µs.

3. The method according to claim 1 wherein a length of said pulse is in the same order as an emission half time of the dye and a repeat frequency of the pulses is lower than $10^7$ $s^{-1}$.

4. The method according to claim 1 wherein at least two low power light sources are used to irradiate said dye.

5. The method according to claim 1 wherein the light source is pulsed mechanically or electronically, and wherein said pulse is focused prior to irradiating said dye.

6. The method according to claim 1 wherein the light source is a semiconductor laser.

7. The method of claim 1, wherein said light pulse has a duration of 0.1 to 1 millisecond.

8. The method of claim 1, wherein said light source is selected from the group consisting of lasers and xenon discharge lamps.

9. The method of claim 8, wherein said light source is either an argon-krypton mixed gas laser or a semiconductor laser.

10. The method of claim 8, wherein said light source is a xenon discharge lamp.

11. The method of claim 1, wherein said light pulse comprises substantially visible light.

12. The method of claim 1, wherein said multi-photon absorption comprises two-photon absorption.

* * * * *